(12) United States Patent
Milbocker et al.

(10) Patent No.: US 12,077,430 B2
(45) Date of Patent: *Sep. 3, 2024

(54) TEXTILES HAVING A MICROSTRUCTURED SURFACE AND GARMENTS COMPRISING THE SAME

(71) Applicant: BVW Holding AG, Cham (CH)

(72) Inventors: Michael Milbocker, Holliston, MA (US); Lukas Bluecher, Eurasberg (DE)

(73) Assignee: BVW Holding AG, Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/125,891

(22) Filed: Mar. 24, 2023

(65) Prior Publication Data

US 2023/0234838 A1    Jul. 27, 2023

Related U.S. Application Data

(63) Continuation of application No. 15/285,529, filed on Oct. 5, 2016, now Pat. No. 11,613,461.

(Continued)

(51) Int. Cl.
    *D06M 23/16*      (2006.01)
    *A41D 19/015*      (2006.01)
    (Continued)

(52) U.S. Cl.
    CPC .... *B81C 1/00206* (2013.01); *A41D 19/01558* (2013.01); *A61B 42/10* (2016.02);
    (Continued)

(58) Field of Classification Search
    CPC ......... B81C 1/00206; A41D 19/01558; D06M 2200/05; D06N 2209/141;
    (Continued)

(56) References Cited

U.S. PATENT DOCUMENTS 6,994,045 B2    2/2006    Paszkowski
7,419,615 B2    9/2008    Strauss
(Continued)

FOREIGN PATENT DOCUMENTS

JP      1995197017 A      8/1995
WO      2016149735      9/2016

OTHER PUBLICATIONS

Search Report of corresponding Chinese Patent Application No. 201680070588.5 dated May 25, 2020, 3 pages.

*Primary Examiner* — Matthew D Matzek
(74) *Attorney, Agent, or Firm* — Patterson Intellectual Property Law, P.C.; Ryan D. Levy; Mark A. Kilgore

(57) ABSTRACT

The present invention relates to textile articles and clothing such as outdoor garments, indoor garments, and commercial protective wear exposed to contact mixtures of water and oil, swimwear and winter wear exposed to mixtures of water and air. At least part of these textile articles possess a surface provided with at least one of 1) a high surface area, 2) hierarchical pattern, 3) contact angles such that hydrophilic portion of a contact mixture possesses a high contact angle and the hydrophobic portion of a contact mixture possesses a low contact angle, and 4) hysteresis angle greater than 5 degrees. Hydrophobic/Hydrophilic contact mixtures of the present invention can be surfaces where water and or ice are present in combination with oil and or air. The textile articles of the present invention resist slippage on surfaces possessing hydrophobic/hydrophilic contact mixtures.

18 Claims, 9 Drawing Sheets

Related U.S. Application Data

(60) Provisional application No. 62/237,460, filed on Oct. 5, 2015.

(51) Int. Cl.
    *A61B 42/10*       (2016.01)
    *B81B 3/00*        (2006.01)
    *B81C 1/00*        (2006.01)
    *A41D 31/12*       (2019.01)

(52) U.S. Cl.
CPC ........ *B81B 3/0067* (2013.01); *B81C 1/00031* (2013.01); *D06M 23/16* (2013.01); *A41D 31/12* (2019.02); *A41D 2600/20* (2013.01); *B81B 2207/056* (2013.01); *D06M 2200/05* (2013.01); *D06N 2209/141* (2013.01); *D06N 2211/103* (2013.01); *D10B 2401/021* (2013.01); *D10B 2401/022* (2013.01); *D10B 2501/041* (2013.01)

(58) Field of Classification Search
CPC ........ D06N 2211/103; D10B 2401/021; D10B 2401/022; D10B 2501/041
USPC .............................. 2/159; 442/79, 85, 86, 118
See application file for complete search history.

(56) References Cited

U.S. PATENT DOCUMENTS

| | | |
|---|---|---|
| 7,887,736 B2 | 2/2011 | Lee et al. |
| 9,120,670 B2 | 9/2015 | Hulseman et al. |
| 9,556,554 B2 | 1/2017 | Lyons et al. |
| 9,908,274 B2 | 3/2018 | Hulseman et al. |
| 9,988,201 B2 | 6/2018 | Darin et al. |
| 10,377,044 B2 | 8/2019 | Hulseman et al. |
| 10,433,924 B2 | 10/2019 | Bluecher et al. |
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,889,005 B2 | 1/2021 | Hulseman et al. |
| 11,051,567 B2 | 7/2021 | Milbocker et al. |
| 2003/0147932 A1 | 8/2003 | Nun et al. |
| 2005/0148984 A1 | 7/2005 | Lindsay et al. |
| 2006/0029808 A1 | 2/2006 | Zhai et al. |
| 2008/0015298 A1 | 1/2008 | Xiong et al. |
| 2008/0241512 A1 | 10/2008 | Boris et al. |
| 2009/0011222 A1 | 1/2009 | Xiu et al. |
| 2009/0076430 A1 | 3/2009 | Simpson et al. |
| 2009/0227164 A1 | 9/2009 | Broch-Nielsen et al. |
| 2010/0021692 A1 | 1/2010 | Bormashenko et al. |
| 2010/0028604 A1 | 2/2010 | Bhushan et al. |
| 2010/0112286 A1 | 5/2010 | Bahadur et al. |
| 2011/0077172 A1 | 3/2011 | Aizenberg et al. |
| 2013/0251948 A1 | 9/2013 | Lyons et al. |
| 2014/0200679 A1* | 7/2014 | Bluecher ................. A61L 31/14 623/23.74 |
| 2014/0276407 A1* | 9/2014 | DeVries ................. A61B 18/16 604/103.08 |
| 2015/0056406 A1 | 2/2015 | Varenberg et al. |
| 2015/0210951 A1 | 7/2015 | Aizenberg et al. |
| 2015/0368838 A1 | 12/2015 | Hulseman et al. |
| 2017/0014111 A1 | 1/2017 | Hulseman et al. |
| 2017/0095019 A1 | 4/2017 | Milbocker et al. |
| 2017/0204279 A1 | 7/2017 | Larimer et al. |
| 2019/0062155 A1 | 2/2019 | Hulseman et al. |
| 2020/0338808 A1 | 10/2020 | Hulseman et al. |
| 2021/0086371 A1 | 3/2021 | Hulseman et al. |

* cited by examiner

TEXTILES HAVING A MICROSTRUCTURED SURFACE AND GARMENTS COMPRISING THE SAME

RELATED APPLICATIONS

This application is a continuation of U.S. patent application Ser. No. 15/285,529 filed on Oct. 5, 2016, which claims the benefit of U.S. provisional application No. 62/237,460 filed on Oct. 5, 2015, the contents of which are hereby incorporated by reference in their entirety.

TECHNICAL FIELD

The present disclosure provides textile articles and clothing such as outdoor garments, indoor garments, medical protective wear, commercial protective wear exposed to contact mixtures of water and oil, swimwear and winter wear exposed to mixtures of water and air. At least part of these textile articles possess a microstructured surface provided with at least one of 1) a high surface area, 2) hierarchical pattern, 3) contact angles such that hydrophilic portion of a contact mixture possesses a high contact angle and the hydrophobic portion of a contact mixture possesses a low contact angle, and 4) hysteresis angle greater than 5 degrees.

BACKGROUND

While this section is largely devoted to established observations and theories, some of the material contained in this section may be new with respect to interpretation or perceived application, nevertheless the underlying theory is known. Thus, we do not intend that ideas disclosed in this section constitute prior art, and that some of the connections made between variant states of prior art may constitute invention.

The interaction of a solid textured surface with water in a gaseous environment is described by the Cassie-Baxter model. In this model, air is trapped in the microgrooves of a textured surface and water droplets rest on a compound surface comprising air and the tops of microprotrusions. The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called superhydrophobic surfaces.

Superhydrophobicity is variously reported as a material exhibiting a contact angle with water that is greater than contact angles achievable with smooth but strongly hydrophobic materials. A hydrophobic surface repels water. The hydrophobicity of a surface can be measured, for example, by determining the contact angle of a drop of water on a surface. The contact angle can be measured in a static state or in a dynamic state. A dynamic contact angle measurement can include determining an advancing contact angle or a receding contact angle with respect to an adherent species such as a water drop. A hydrophobic surface having a small difference between advancing and receding contact angles (i.e., low contact angle hysteresis) results in surfaces with low resistance to in plane translation (low adherence). Water can travel across a surface having low contact angle hysteresis more readily than across a surface having a high contact angle hysteresis, thus the magnitude of the contact angle hysteresis can be equated with the amount of energy needed to move a substance.

The classic motivation from nature for surface texture research is the lotus leaf, which is superhydrophobic due to a hierarchical structure of convex cell papillae and randomly oriented hydrophobic wax tubules, which have high contact angles and low contact angle hysteresis with water and show strong self-cleaning properties.

A lesser known motivation from nature is the red rose petal, with a hierarchical structure of convex cell papillae ornamented with circumferentially arranged and axially directed ridges, which have a moderate contact angle and high angular contact difference. The contact angle is a measure of the amount of water directly in contact with the textured surface, while the contact angle hysteresis is a measure of the degree to which water is mobile on a surface.

The evolutionary motivation for each of these states is quite distinct. In the case of the lotus leaf, and botanical leaves generally, minimal contact with water and high water mobility results in preferential adherence of the water to particulate contaminants, which are cleared from the leave as the water runs off. This serves to reduce to the amount of light absorbance by surface contaminants, and increase photosynthetic efficiency. In the case of the rose petal, and botanical petals generally, most pollinators are attracted to high tension water sources which provide ready accessibility without drowning the insect. Thus, high contact angle paired with high contact angle hysteresis is preferred where the evolutionary stimulus is reproduction in botanicals, and high contact angle paired with low contact angle hysteresis is preferred where the evolutionary stimulus is metabolism and growth.

Considering for a moment a single texture scale, when water is placed on a textured surface it can either sit on the peaks of the texture or wick into the valleys. The former is called the Cassie state, and the later the Wenzel state. When the Wenzel state is dominant, both the contact angle and contact angle hysteresis increase as the surface roughness increases. When a roughness factor exceeds a critical level, however, the contact angle continues to increase while the hysteresis starts decreasing. At this point, the dominant wetting behavior changes, due to an increase in the amount of hydrophobic component (in this case, air) at the interface between the surface and water droplet.

When multiple texture scales are employed, some can be Wenzel and others Cassie. Of the two states, the Wenzel state has the lower contact angle, higher contact angle hysteresis and lower mobility. In mixed Wenzel-Cassie states it is possible to have high contact angle and high contact angle hysteresis. However, the hydrophobicity of a textured solid relative to the interacting hydrophobic and hydrophilic components is very important.

Water possesses a dipole structure which makes it attractive to any other substance that is charged. Molecules with a charge surplus localized at a specific location on the molecule renders that molecule hydrophilic. In the case of polymers, the charges can associate, and the bulk substance and possess a macroscopic charge. And in such macroscopic assemblages, such materials are strongly water attractive. And when those macroscopic charge localities are associated with surface texture, than a substance becomes superhydrophilic.

The term superhydrophilic has various meanings in the literature, and in many cases simply refers to the rendering of a substance more hydrophilic, or a decrease in contact angle relative to a flat surface of the same substance. Here, it is meant the accentuation of surface charge and surface energy such that water is always bonded to the substrate surface, even though any particular water molecule may have a short residence time on the polymer surface. This has a commercial advantage in that the adherent surface of the present textiles is both shielded from contaminating debris and also is self-washing due to the stochastic attachment/detachment of water molecules from the surface.

In the botanical world, most textured surfaces occur on substrates that are hydrophobic. However, when a hydrophobic fluid replaces the water, a Cassie state can easily be converted to a Wenzel state. This is not always the case, and depends on the vapor pressure and viscosity of the hydrophobic material and how quickly the air trapped in the surface texture can be dissipated.

Various attempts have been made to achieve hydrophobic coatings and surfaces, as follows: U.S. Pat. No. 6,994,045 describes a superhydrophobic coating acting as a substrate for a gaseous lubricant of very low viscosity, has a hierarchical fractal structural of the surface wherein the forms of the first hierarchical level are located at the coating's substrate, and the forms of each successive hierarchical levels are located on the surface of the previous hierarchic level and the forms of individual higher hierarchic levels reiterate the forms of the lower hierarchic levels. U.S. Pat. No. 7,419,615 discloses a method of forming a superhydrophobic material by mixing a hydrophobic material with soluble particles to form a mixture. U.S. Pat. No. 7,887,736 discloses a superhydrophobic surface repeatedly imprinted using a template, so that mass production of a superhydrophobic polymer over a large area can be economically implemented. U.S. Pub. No. 20030147932 discloses a self-cleaning or lotus effect surface that has antifouling properties. U.S. Pub. No. 20060029808 discloses a coating that can remain superhydrophobic after being immersed in water for one week. U.S. Pub. No. 20080015298 discloses a superhydrophobic coating composition. U.S. Pub. No. 20080241512 discloses a method of depositing layers of materials to provide superhydrophilic surface properties, or superhydrophobic surface properties, or combinations of such properties at various locations on a given surface. U.S. Pub. No. 20090011222 discloses a method of applying lotus effect materials as a superhydrophobic protective coating for various system applications, as well as the method of fabricating/preparing lotus effect coatings. U.S. Pub. No. 20090076430 discloses a bandage that includes a material, which can be breathable, having a first surface, and a plurality of superhydrophobic particles attached to the first surface. The material can have a second surface opposite the first surface that is hydrophilic. U.S. Pub. No. 20090227164 discloses a superhydrophobic coating of a nonwoven material is coated with a spongy mesh structure in the texture and nano ranges. U.S. Pub. No. 20100112286 discloses control and switching of liquid droplet states on artificially structured superhydrophobic surfaces. U.S. Pub. No. 20100021692 discloses a method of manufacturing a multiscale (hierarchical) superhydrophobic surface is provided. The method includes texturing a polymer surface at three size scales, in a fractal-like or pseudo fractal-like manner, the lowest scale being nanoscale and the highest microscale. U.S. Pub. No. 20100028604 discloses a superhydrophobic structure comprise a substrate and a hierarchical surface structure disposed on at least one surface of the substrate, wherein the hierarchical surface structure comprises a microstructure comprising a plurality of microasperities disposed in a spaced geometric pattern on at least one surface of the substrate. U.S. Pub. No. 20110077172 discloses a method of localized deposition of a material and includes a superhydrophobic substrate comprising raised surface structure In view of the above, there is a need for adherent textile materials comprised of textures that create Cassie and Wenzel states when exposed to a surface having hydrophobic/hydrophilic mixture. Such textile materials are particular useful for garments particularly those used in medical settings, such as surgical gloves.

BRIEF SUMMARY

The present invention relates to textile articles or clothing, such as garments that contact ice or mixtures of oil and water, including medical wear, particularly surgical or protective gloves. Indoor fabrics which are exposed to wet skin and soap solution, such as a slip-free surface lining a bath tub, or a bathroom floor surface in contact with wet skin. Outdoor fabrics or surfaces such as industrial gloves in contact with oil-water mixtures, footwear in contact with ice or water mixed with a lubricant such as motor oil. The present adhesive textiles are nonslip surfaces and can be characterized as possessing high surface area compared with a smooth surface of the same dimensions.

A scale of interaction is defined by the surface texture of the present adhesive textile, and is typically hierarchical, and characterized by at least two spatial scales, one on the order of micrometers (microns) and another on the order of 100 s of microns. The surface texture may induce one state with a large difference between preceding and receding contact angles (contact angle hysteresis), or alternatively another state with a small contact angle hysteresis. States of interest are known respectively as Wenzel and Cassie states. Each of the hierarchical spatial scales may induce separately a Wenzel or Cassie state, such that combinations are possible on a multiplicity of spatial scales.

These states are phenomena between hydrophobic and hydrophilic components of a mixture residing at a textured surface interface. In the Cassie state the adherent textile is resistant to hydrophobic debris adhesion, for example oil in an oil water mixture. In the Wenzel state the implant is reversibly adherent to a hydrophilic surface, for example a wet or ice surface. In hybrid Cassie-Wenzel states, where one texture scale is Wenzel and the other is Cassie, the adherent textile can be both localizing to a wet surface and resistant to hydrophobic contaminants such as oil. The interaction of a solid textured surface with water in a gaseous environment is described by the Cassie-Baxter model. In this model, air is trapped in the micro-grooves of a textured surface and water droplets rest on a compound surface comprising air and the tops of microprotrusions.

The importance of a fractal dimension between multiple scales of texture is well recognized and many approaches have been based on the fractal contribution, i.e., the dimensional relationship between different scales of texture. However, regardless of the material (organic or inorganic) used and geometric structure of the surface texture (particles, rod arrays, or pores), multiple scales of texture in combination with low surface energy has been required to obtain the so called superhydrophobic surfaces.

Superhydrophobicity is variously reported as a material exhibiting a contact angle with water that is greater than contact angles achievable with smooth but strongly hydrophobic materials. The consensus for the minimum contact angle for a superhydrophobic substance is 150 degrees, so in this context most of the embodiments of the present invention are not strictly superhydrophobic, although this option is not excluded. The reason for this is that a Wenzel-Cassie state lies in its hydrophobicity between nontextured surfaces and surface that generate a Cassie-Baxter interface. In optimizing the adherence of the textiles of the present invention superhydrophobicity is just one aspect of a number of interesting texture controlled mechanisms, and in this context the contact angle is less important than the contact angle hysteresis.

The high surface area is achieved by superimposing multiple structures one on top of the other in superposition. When these multiple structures are sufficiently different in dimension then the superposition of these structures is referred to as a hierarchical structure or pattern. A subset of surfaces useful in the present invention are characterized as superhydrophobic. A superhydrophobic surface is any surface with which a drop of water makes a contact angle greater than 120 degrees. A hydrophobic/hydrophilic contact mixture is a liquid/solid mixture or liquid/gas mixture in which first component of solid, liquid or gas is more hydrophilic than the second component of solid, liquid or gas.

The present inventors have surprisingly discovered that a microstructured surface of the present invention adhesively interacts with a surface comprised of a hydrophobic/hydrophilic contact mixture. These surfaces create a nonslip contact with a great variety of slippery, slimy or otherwise slick surfaces.

In particular the present invention relates to textiles having at least part of their surface coated with a thin, well adherent, porous or nonporous coating with super hydrophobic properties. The static water contact angle values, measured on a smooth and plane surface, is higher than about 120°, preferably higher than 130°, more preferably higher than 150°.

For example, textiles being treated with this method have their hydrophobicity markedly improved. They can for example provide improvements in water repellency, soil/dirt sticking prevention, reduced buildup on surface or not detrimental to water vapor/air permeability. Additionally, the present surfaces differ from many superhydrophobic surfaces in that they establish a Wenzel-Cassie interface comprising the hydrophobic/hydrophilic contact mixture. While the hydrophobic component of the contact mixture is attracted to the surface the hydrophilic component of the contact mixture is repelled. The result is that under shear stress, the two surfaces in contact resist relative motion due to the difference in the contact angles of the leading and trailing edges. This difference in leading and trailing contact angles represents and energy difference which must be overcome before slippage occurs.

The textile substrates of interest for the present invention may include a wide range of materials in the form of webs, tapes, films, animal skin like leather or fur, woven and nonwoven layers; they can be porous or nonporous, rigid or flexible, made of polymers, natural or synthetic fibers, leather, biodegradable materials, or any conventional material used in making textiles or products comprising textiles for outside use. In one embodiment, medical or surgical gloves advantageously comprise the microstructured surface textures describes herein.

When organic synthetic resins are chosen, such substrate materials could be fabricated from polyethylene, polyacrylics, polypropylene, polyvinyl chloride, polyamides, polystyrene, polyurethanes, polyfluorocarbons, polyesters, silicone rubber, hydrocarbon rubbers, polycarbonates and other synthetic polymers. A particularly preferred polymeric substrate is polyethylene or polypropylene as used e.g. in the manufacture of nonwoven textile substrates. To these textiles is adhered a thin layer of solvent cast, polymerized, or melt cast polymer capable of being impressed with the hierarchical patterns of the present invention.

Alternatively a more conventional thin film coating process followed by high energy surface curing can be used. In this method a high speed vacuum coating process for producing durable and thin water repellent coatings on a textile substrate is that can be impressed with the hierarchical pattern during formation.

A pattern transference process may include a movable support such as rotating drum in a vacuum chamber. The surface of the support is maintained at a temperature sufficient to permit condensation of a vaporized material deposited in the chamber. The material is a curable monomer with a relatively low molecular weight. The monomer vapor is created using a flash vaporizer. The desired amount of curable monomer is metered to a heated flash vaporizer system where the material is vaporized. It is then transported e.g. by its inherent pressure, to the textile substrate resting on the rotating drum and condensed on the surface of the textile substrate. At the same time the drum is impressed on an adjacent drum possessing the hierarchical pattern. According to the method the textile substrate is then transported to a curing means such as an energy source which emits an electron beam, UV light radiation or exposure to an electromagnetic field. Alternatively, the curable monomer can also be transferred into radicals by passing through a plasma. The curing of the monomer by the curing means before, during or after the hierarchical pattern is transferred then provides a coating on the textile substrate surface which has a static water contact angle of more than 120°. The hierarchical pattern forms a Wenzel-Cassie interface between the hierarchical pattern and a hydrophobic/hydrophilic contact mixture.

DETAILED DESCRIPTION OF THE INVENTION

Figure 1:
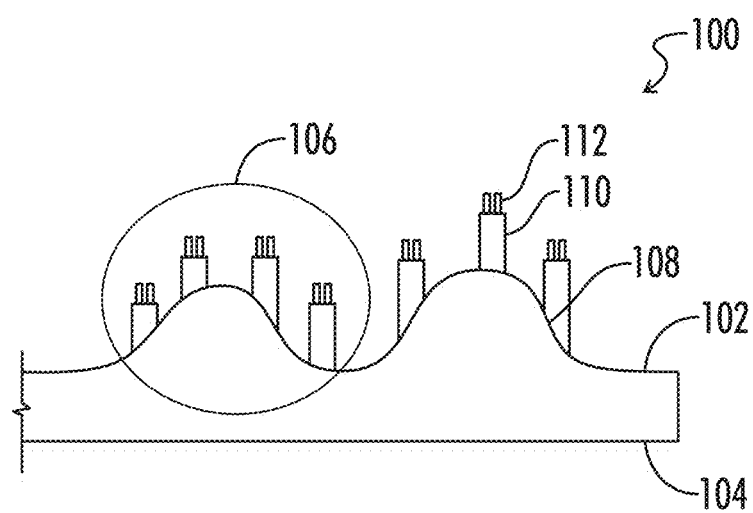
FIG. 1 depicts an embodiment of a microstructured surface useful for an adhesive textile.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that must be included in all embodiments, unless otherwise stated.

The present invention relates to textiles with surfaces comprised of textures that initially create Cassie and Wenzel states when exposed to an aqueous environment comprising a hydrophobic component. The hydrophobic component can be a liquid such as an oil or a gas such as ambient air. These states evolve as a result of an interface comprised of a hydrophobic/hydrophilic mixture. We have discovered the liquid hydrophobic/liquid hydrophilic mixture creates an interface analogues to the typical Wenzel-Cassie State that develops on an water/air mixture. In the modified Wenzel-Cassie state, the trapped phase analogous to the classical gaseous phase is the liquid hydrophobic phase Referring now to FIG. 1, generally a surface for an adhesive textile 100 of the present invention possesses a hierarchical surface 106 comprised of a large scale structure with a plurality of protuberances and depressions disposed in a geometric pattern on at least one surface of a substrate 108, and a medium scale structure 110 disposed on at least one surface of the large scale level structure 108 is comprised of protuberances 112. The small scale structure 114 is similarly comprised of protuberances 116 and depressions 118 disposed on the medium scale structure 110. The large scale protuberances 108 should be high enough so that a hydrophilic component of a hydrophobic/hydrophilic contact mixture does not touch the large scale depressions between adjacent protuberances 108. In the embodiment of FIG. 1, the large scale protuberances 108 may comprise a height H of between about 25 to about 1000 microns and a diameter D of between about 25 to about 2000 microns, wherein the fraction of the surface area of the substrate 108 covered by the protuberances 104 may range from between about 0.1 to about 1.0. The medium scale protuberances 110 may comprise a height 120 of between 5 to about 25 microns and a diameter 122 of between 5 to about 50 microns, wherein the fraction of the surface area of the substrate 108 covered by the protuberances 110 may range from between about 0.1 to about 0.9. The small scale structure 112 may be disposed primarily on the medium scale structure 110.

The arrangement of hierarchical structures may be geometric and describable generally with a mathematical equation. Alternatively, the hierarchical structures may be randomly disposed, possibly with varying pitch, which is more typical of natural structures. The arrangement of hierarchical structure can generally be described by a fractal dimension. A fractal dimension is a statistical quantity that gives an indication of how completely a collection of structures appears to fill space, in the present case a plane, as one examines that structure on a multiplicity of spatial scales. Specifying a fractal dimension, which is statistical in nature, does not necessarily indicate that the hierarchical structure is well defined by a mathematical equation. Generally, a random arrangement of structures within a specific scale possesses a higher fractal dimension than one in which the structure is mathematically described at all points on a surface. Thus, a random structure may possess an advantage in the aspect that a adhesive surface of the present invention has greater utility when interacting with a natural surface. A higher fractal dimension within a specific spatial scale may be achieved by applying to a substrate multiple pitch arrangements. The protuberances and depressions may be locally scaled with respect to the local pitch. Accordingly, the pitch may vary within a scale structure. In the practical realization of higher fractal dimension structures, the variation of the pitch may be describable by a mathematical equation, for example, a sinusoidal variation of pitch, which would have utility in mimicking natural surfaces.

Generally, structures can be described as sharp-edged or rounded, and this feature is not typically captured by a fractal dimension. Another structural aspect not addressed by the above descriptive parameters is the degree of communication between structures. By communication, it is meant that a structure, such as a protuberance or a depression, has a spatial extent greater than the pitch. For example, a valley surrounding a protuberance may be connected to another valley surrounding another protuberance, thus the depressions are said to be communicating whereas the protuberances are not. The communication may range from 1 to about 1000, more particularly the communication may extend over the entire surface of the substrate.

These structures are constructed with the purpose of creating Wenzel and Cassie states, on a multiplicity of scales, when the adhesive textile of the present invention comes in contact with a hydrophobic/hydrophilic contact mixture. It is known in the art that the transition to the Wenzel state can be discouraged by the use of sharp cornered features in the plane of the surface. However, the occurrence of sharp cornered structures in natural structures, such as rose petals, is less common. Natural structures tend to possess rounded surface features, especially radiused or filleted corners. In nature, resistance to conversion to a Wenzel state seems to involve the creation of involute rounded structures rather than sharp edges. By involute it is meant concavity oriented in a line not orthogonal to the substrate surface. Such structures are difficult to create by an etching or casting method, but can readily be created by an embossing method that entails folding of a structure. Similarly, the Wenzel state can be discouraged by the use of curving communications between structures as opposed to straight line communication. In most cases, higher hydrophobicity equates with lower propensity for a Wenzel transition.

The hydrophobicity of a surface is enhanced by the placement of exterior corners around depressions. In some embodiments, this is achieved by the creation of additional pairs of adjacent depression walls that project into and are joined at the interior of the depression. In some embodiments this is achieved by designing an ordered array of depressions of a first hierarchy (examples: triangular, rectangular, pentagonal, or hexagonal shapes, regular or irregular; and further polygonal shapes defined generally by straight line segments). A second feature of smaller size and different hierarchical order is then superimposed on the depression wall of the first pattern. The method employed in creating such a structure may involve first emboss a large scale structure and then secondarily emboss additional smaller scale structure, preferably smaller scale structure embossed on larger scale structures.

The methods of manufacture of nonwoven adhesive textiles of the present invention include lithography, casting, extrusion/embossing, and any of several methods for transferring a texture to a surface. A preferred method is embossing, where a polymeric substance is heated to a molten state and passed through dual rollers, at least one of which contains a negative image of the desired embossed structure. A small scale texture is embossed on a planar sheet. This embossed planar sheet is heated to a malleable but not fluid state and passed through dual rollers possessing a medium scale texture which impresses an inverse image. This process can be repeated multiple times. The medium scale texture is large relative to the small scale texture, thus the impression of the medium scale texture folds the small scale texture, making possible involute structures which would ordinarily not be possible with a lithography or casting method. Methods for forming such hierarchical microstructured surfaces useful in the present disclosure are described in U.S. application Ser. No. 14/802,632, which is hereby incorporated by reference in its entirety.

The adhesive textiles of the present invention have three or more levels of textures assembled in a manner to yield a high surface area while maintaining a minimum spacing between textures to allow for liquid flow and penetration to promote in the first instance surface washing and in the second instance surface adhesion; and while maintaining a minimum structural strength obtained by keeping height to width aspect ratio of all features below a critical level at which material strength is exceeded.

Figure 2:
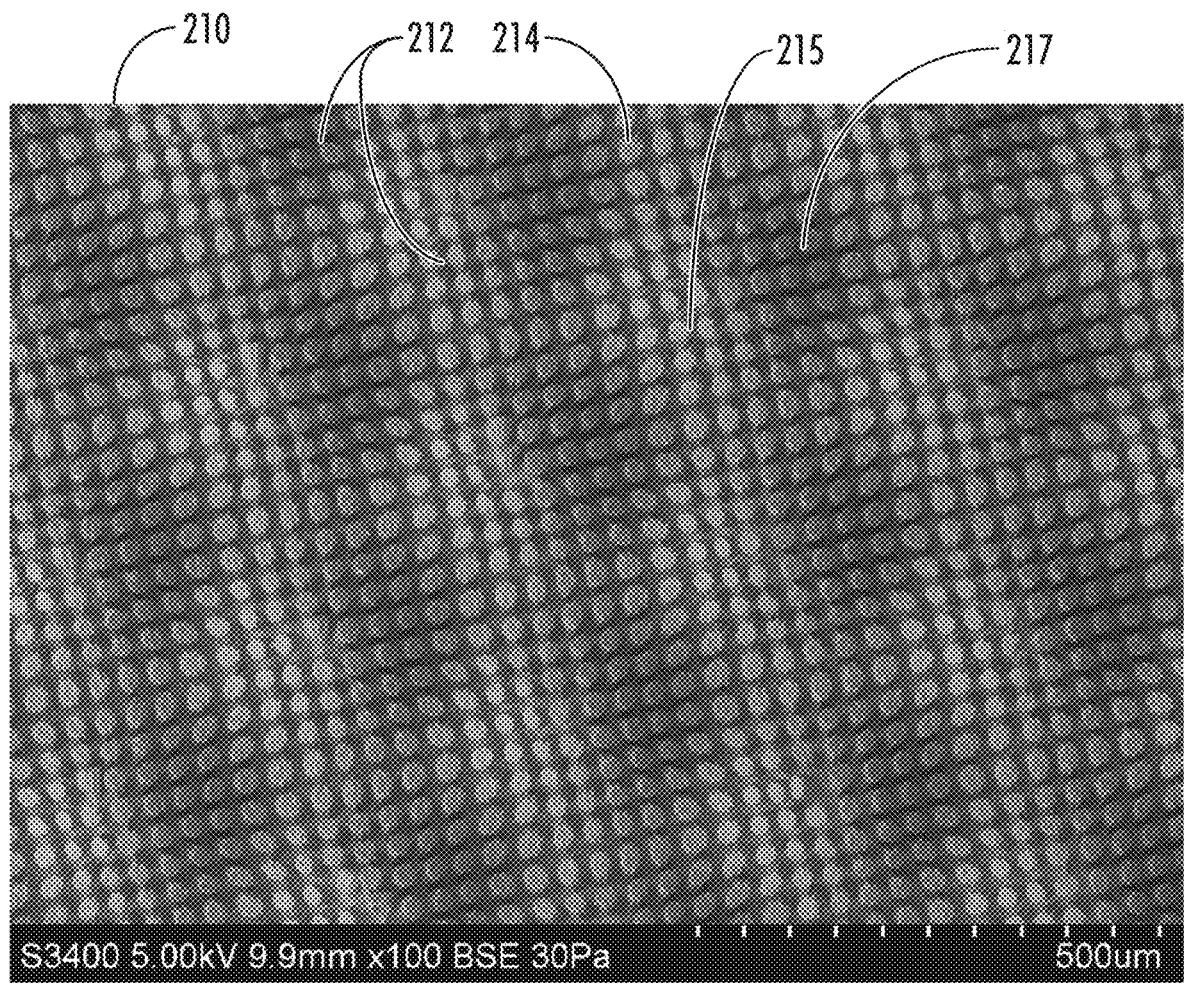
FIG. 2 is an image of an embodiment of surface useful for adhesive textile.

Referring to FIG. 2, a first embodiment of a textural arrangement on a textile surface according to the present invention is shown comprising a substrate, designated generally as 210. In the illustrated embodiment, substrate 210 has a sinusoidal waveform comprising a series of rounded peaks and valleys that produce a continuously curving surface across at least a portion of substrate 210. The sinusoidal waveform of substrate 10 defines a first set of large scale features, designated generally as 212. In FIG. 2, substrate 210 is constructed and arranged to focus on a series of rounded knobs forming peaks 215 projected upwardly from the surface with associated valleys 217 disposed between peaks 215.

Figure 3:
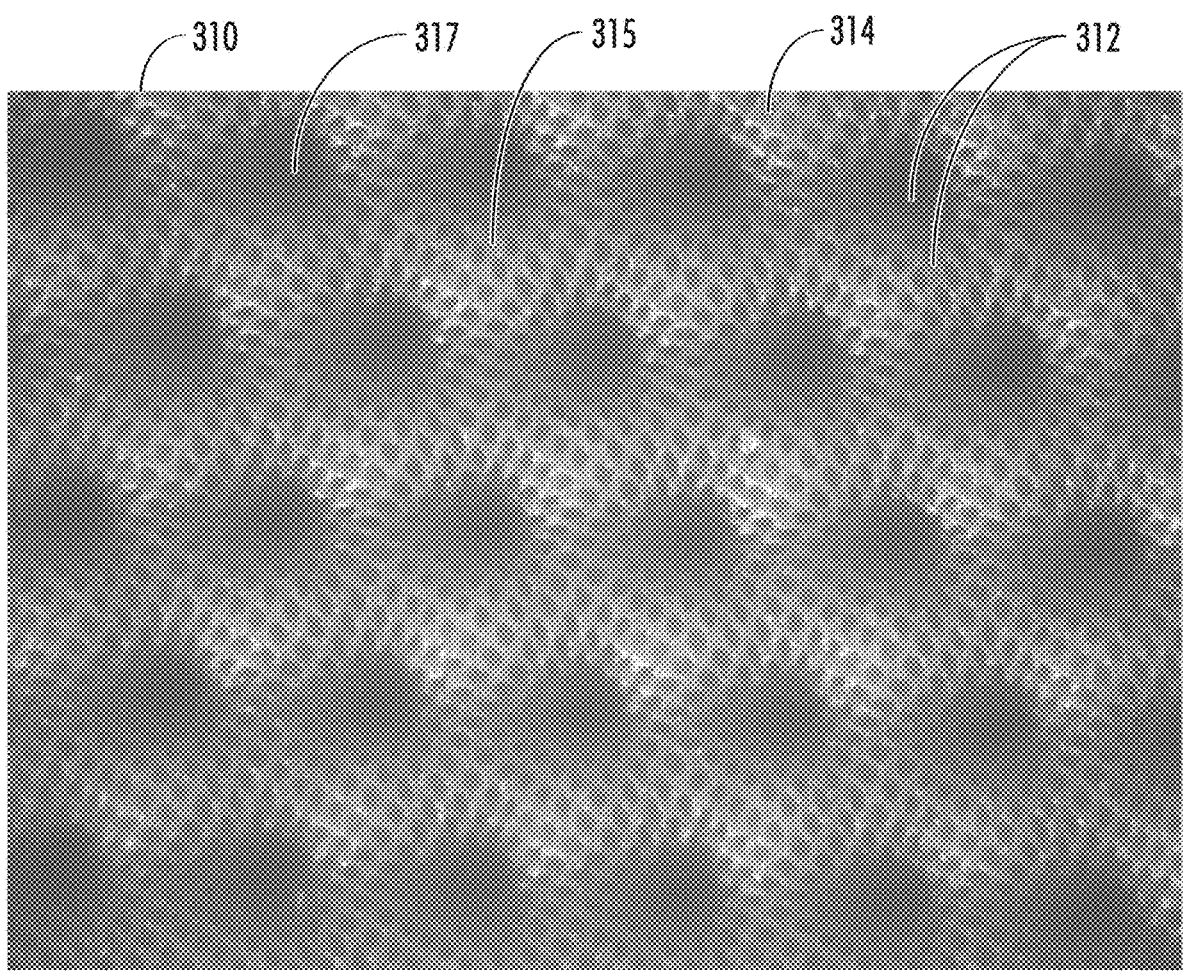
FIG. 3 is an image of an embodiment of microstructured surface having an inverse pattern.
Figure 4A:
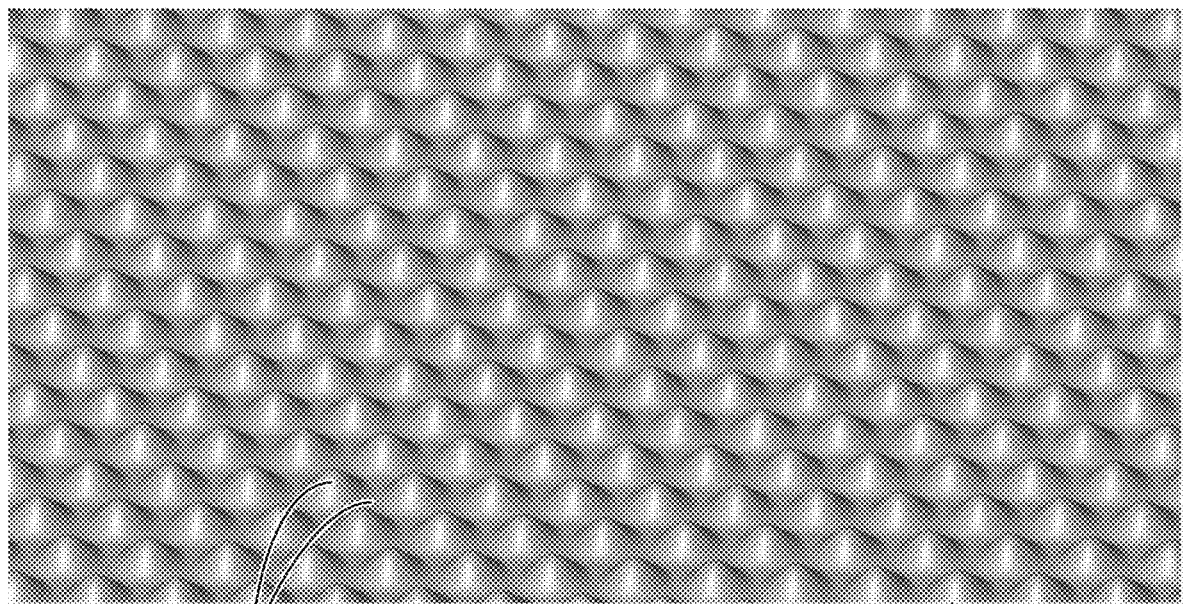
FIGS. 4A-4D depict a selection of substrates 410 having various sinusoidal waveform patterns that provide alternative curved surface texture features across substrate 410.
Figure 4B:
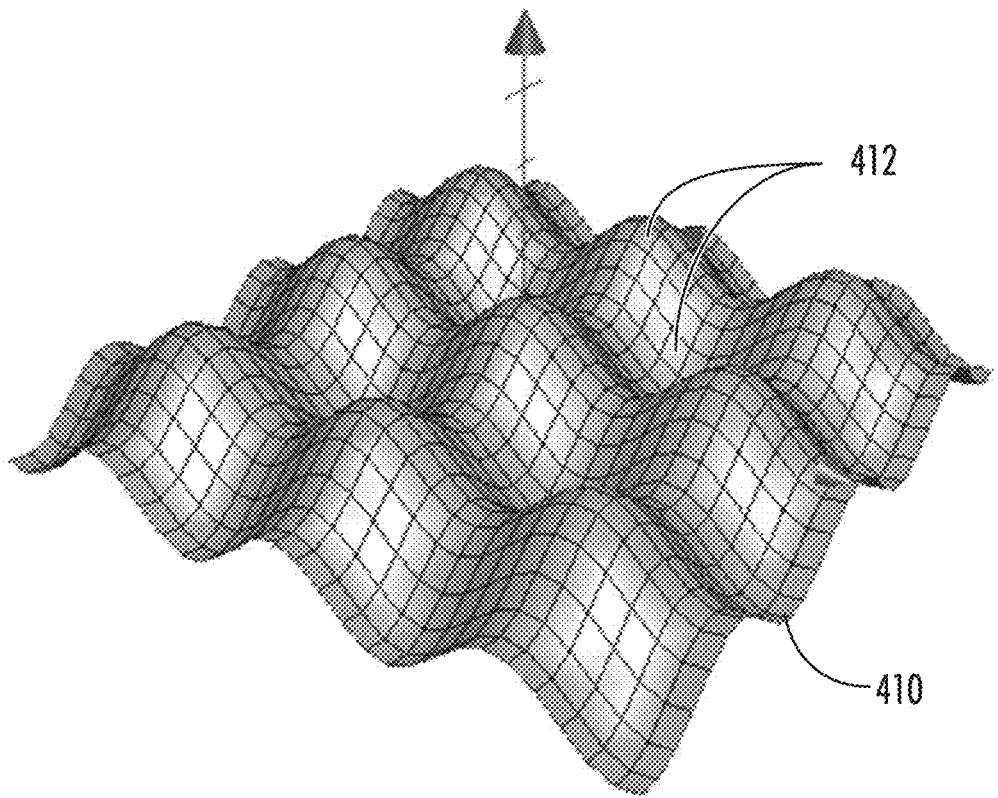
Figure 4C:
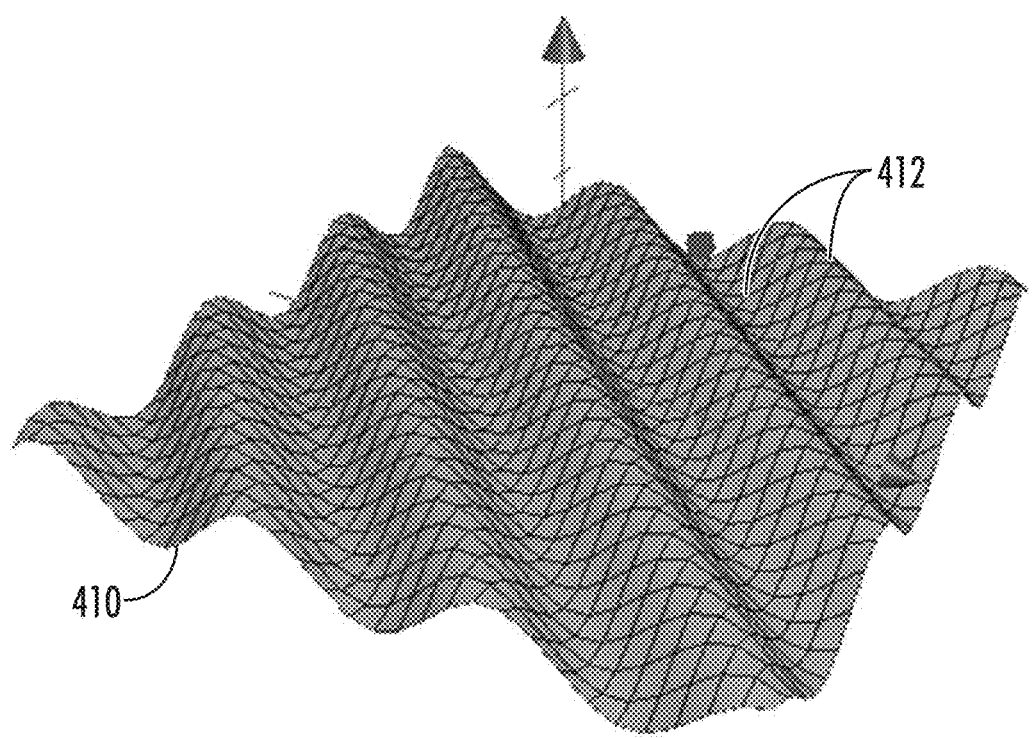
Figure 4D:
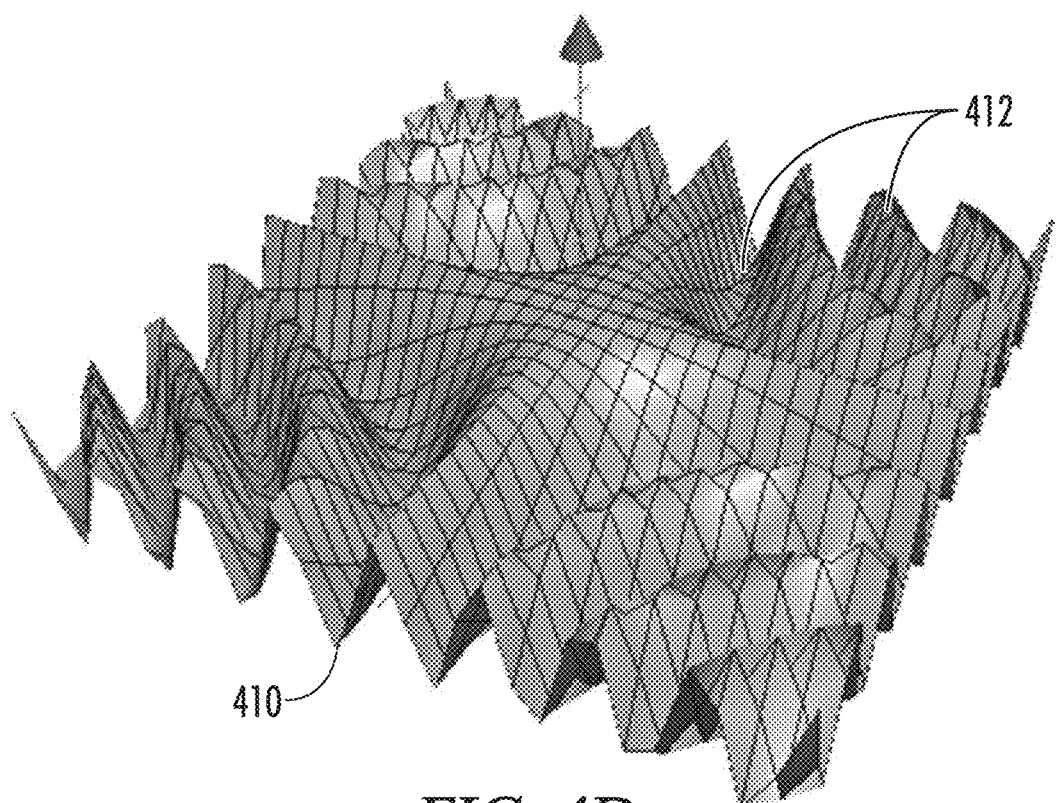

In a second embodiment shown in FIG. 3, the inverse arrangement is shown in which substrate 310 is constructed and arranged to focus on a series of rounded cavities forming valleys 317 extending inwardly into substrate 10 as the dominant feature with the associated peaks 315 disposed between valleys 317. In both embodiment, the surface of substrate 310 is continuously curving throughout sinusoidal waveform pattern area.

According the present invention, the term sinusoidal waveform as used herein refers to a surface having a repetitive oscillation of rounded, nonflat curvature described by mathematical formulas incorporating trigonometric functions sine, cosine, tangent or exponential and power series functions. These mathematical formulas are used in computer aided design and computer aided manufacturing software to create texture surfaces using rapid prototyping, milling, electrical discharge machining or similar techniques to create a polymer or metal surface with the sinusoidal waveform texture features. The advantage of using mathematical formulas is that large numbers of rounded, nonflat features can be created rapidly in computer aided design and computer aided manufacturing software. Texture features of this type cannot be created using lithographic techniques.

Referring to FIGS. 4A-4D, a selection of substrates 410 are shown having various sinusoidal waveform patterns that provide alternative curved surface texture features across substrate 410. These embodiments are for illustrative purposes only as example embodiments of substrate 410 and are not limiting of the present invention and the term sinusoidal waveform as used herein.

According to the present invention, first set of texture features 412 includes dimensions selected from a size within a range of about 100 microns to about 1000 microns. More specifically as will be detailed herein below, in a preferred embodiment, the sinusoidal waveform is arranged so that first set of texture features 12 has sinusoidal rounded cavities of 750 microns, a pitch of 750 microns, and a depth of about 240 to 500 microns. This arrangement of the substrate is intended to promote an adhesive Wenzel-Cassie state with a hydrophobic/hydrophilic contact mixture.

Figure 5:
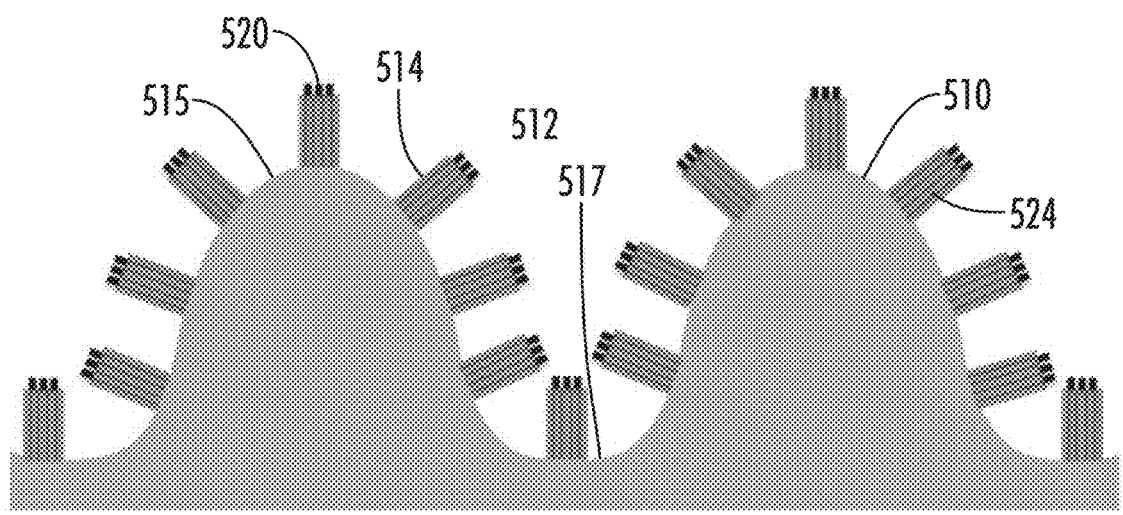
FIG. 5 depicts a side view of an embodiment of the microstructured surface on a substrate according to the present disclosure having a second set of features disposed on the surface of the substrate.
Figure 6:
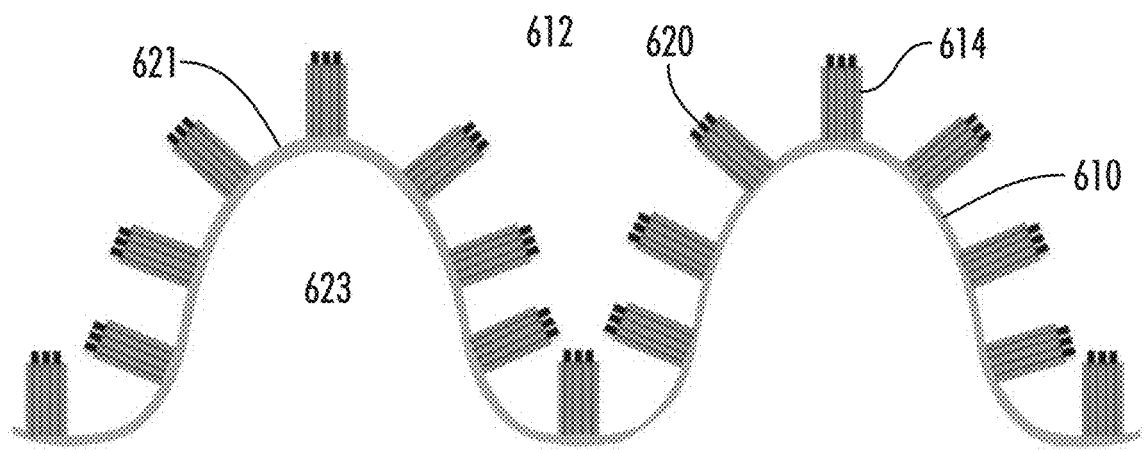
FIG. 6 depicts a side view of another embodiment of the microstructured surface on a thin film substrate according to the present disclosure.

Referring to FIG. 5, a second set of texture features 514 is disposed on the surface of substrate 510. In one embodiment, second set of texture features 514 is molded on first set of texture features 512 of substrate 510. As detailed herein below, in a preferred embodiment, substrate 510 is a compression molded polymeric material in which first and second sets of texture features 512, 514 are formed on substrate 510 during a single molding step. First and second sets of texture features 512, 514 cooperate to increase the surface area and affect at least one of adhesion, friction, hydrophilicity and hydrophobicity of substrate 510.

Preferably, the compression molded polymeric material forming substrate 510 is a environmentally durable polymer. In one embodiment, substrate 510 comprises polyethylene-nylon copolymer. In the illustrated embodiments, second set of texture features 514 is selected from the group consisting of microstructured projections and microstructured cavities, and combinations thereof. The illustrated embodiment in FIG. 3, second set of texture features 314 comprise microstructured cavities extending downwardly into substrate 310.

Further in FIGS. 5-8, a second set of texture features 514, 614, 714 and 814 comprise microstructured projections extending upwardly from substrate 510, 610, 710 and 810, respectively. Preferably, in the illustrated embodiments of FIGS. 5-8, the microstructured projections of said second set of texture features 514, 614, 714, 814 comprise generally cylindrical pillars.

Preferably, in the illustrated embodiment of FIG. 3, the microstructured cavities of second set of texture features 314 comprise generally cylindrical recesses. Referring to FIG. 5, in one embodiment in which substrate 510 is a thin film substrate and has operable opposing top and bottom surfaces, first set of texture features 512 disposed on a top surface 521 of substrate 510 form a complementary shape on a bottom surface 523 of substrate 510 so that a rounded peak on top surface 521 forms a rounded valley on bottom surface 523 and the rounded valley on top surface 521 forms a rounded peak on bottom surface 523.

Referring again to FIG. 5, in an embodiment in which substrate 510 is a thin film substrate and has operable opposing top and bottom surfaces, second set of texture features 514 includes a series of microstructured projections on one of top surface 521 and bottom surface 523 of substrate 510, which then define a series of complementary microstructured cavities on the other of said top surface and said bottom surface 521, 523. Likewise, in an embodiment in which second set of texture features 514 comprises microstructured cavities which project downwardly through substrate 510 from a top surface 521, they form complementary microstructured projections on the opposing bottom.

Referring to FIGS. 2 and 5, in the illustrated embodiments, second set of texture features 214, 514 include at least a portion of texture features that extend along an axis normal to the curve of the sinusoidal waveform of substrate 210 and 510, respectively, at a given point for the individual microstructure. In this way, second set of texture features 214, 514 follow the curvature of first set of texture features 212, 512.

According to the present invention, second set of texture features 514 includes dimensions selected from a size within a range of about 10 microns to about 100 microns. Further, second set of texture features 514 preferably have a height to width aspect ratio of less than 5, and a minimum spacing of 1 micron between each texture feature of said second set of texture features to maintain structural strength while allowing for liquid flow and penetration between the individual microstructures comprising second set of texture features 214.

Referring again to FIGS. 5-8, a third set of texture features 520, 620, 720, 820 may also be disposed on substrate 510, 610, 710, 810, respectively. Preferably, third set of texture features 520, 6120, 720, 820 is selected from the group consisting of microstructured projections and microstructured cavities, and combinations thereof. In one embodiment, the microstructured projections of third set of texture features comprise generally cylindrical pillars.

Referring again to FIG. 3, in one embodiment, the microstructured cavities of third set of texture features 320 comprise generally cylindrical recesses. Preferably, third set of texture features 320 are compression molded simultaneously with first and second sets of texture features 312, 314. In a further preferred embodiment, third set of texture features 320 have a height to width aspect ratio of less than 5, and a minimum spacing of 1 micron between each texture feature of third set of texture features 320 to maintain structural strength while allowing for liquid flow and penetration between said third set of texture features. The aspect ratio is smaller when devices are made of lower strength materials and larger when made from stronger materials. The spacing between features is smaller for less viscous liquids and larger for more viscous.

Referring to FIGS. 2 and 5, in the illustrated embodiments, third set of texture features 220 and 520 include at least a portion of texture features that extend along an axis normal to the curve of the sinusoidal waveform of substrate 210 and 510, respectively. For purposes of the present invention in which the second and third sets of texture features 214, 514, 220, 520 extend along an axis normal to the curve of the sinusoidal waveform, the normal line to a curve is the line that is perpendicular to the tangent of the curve at a particular point. In the illustrated embodiments, second set of texture features 214, 514 is smaller than first set of texture features 212, 512 and third set of texture features 220, 520 is smaller than second set of texture features 214, 514.

According to the present invention, third set of texture features 220 includes dimensions selected from a size within a range of about 1 micron to about 10. Referring to FIGS. 5-8, in one embodiment, the third set of texture features are disposed on an end surface 522, 622, 722, 822 of second set of texture features 14.

In a further advantageous embodiment, third set of texture features 520, 620, 720, 820 are disposed on first set of texture features 512, 612, 712, 812 between second set of texture features 514, 614, 712, 814. In a further advantageous embodiment, third set of texture features 520, 620, 720, 820 are disposed on an end surface 522, 622, 722, 822 of second set of texture features 514, 614, 712, 814. as well as, disposed on first set of texture features 512, 612, 712, 812 between second set of texture features.

Figure 7:
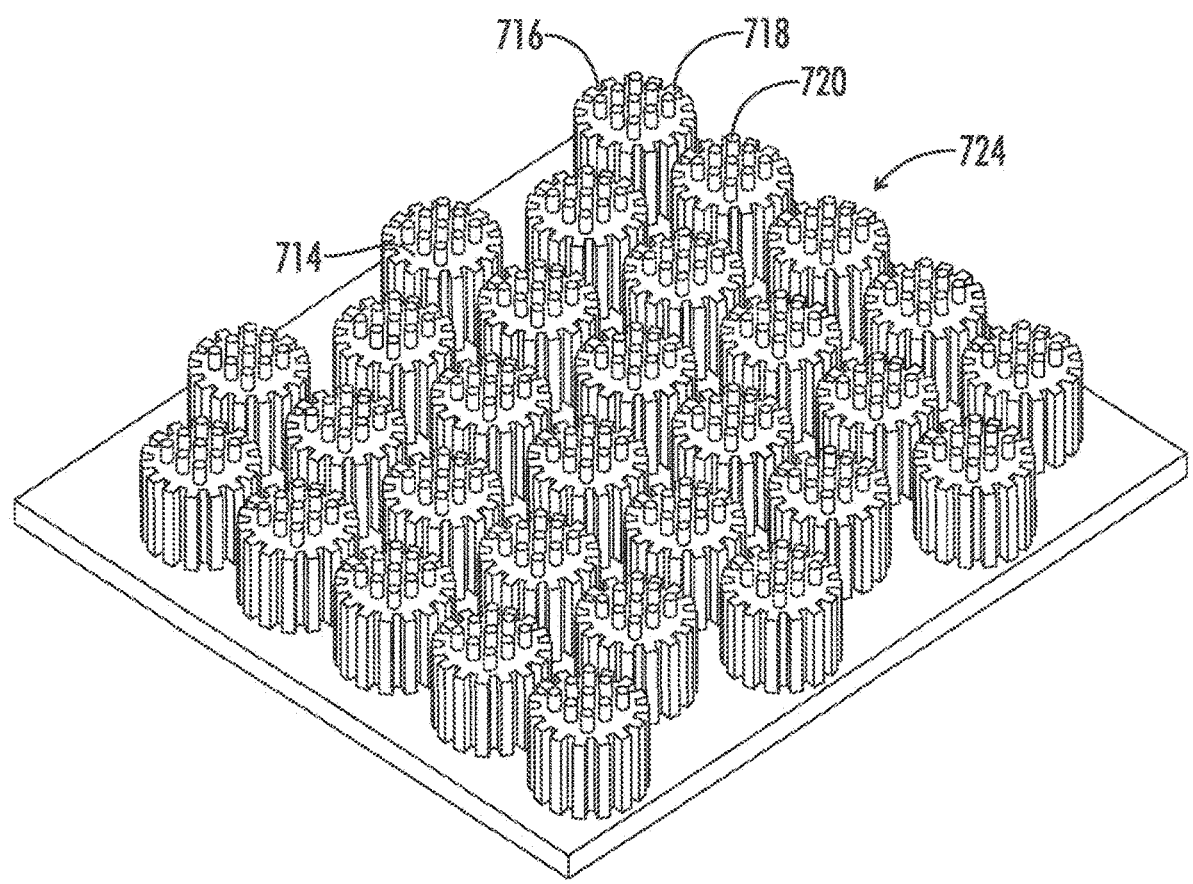
FIG. 7 depicts a perspective view of a microstructured surface having a fourth set of microfeatures.
Figure 8:
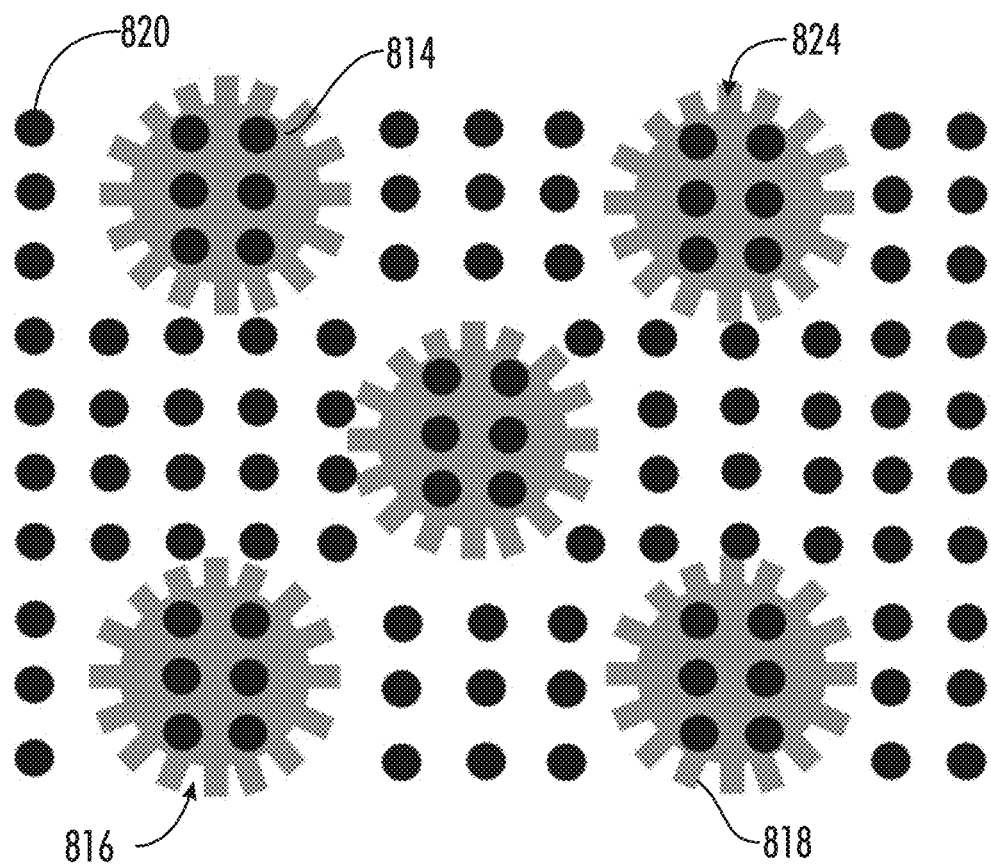
FIG. 8 depicts a schematic top view of a microstructured surface having a fourth set sets of microfeatures.

Referring to FIGS. 7, a fourth set of texture features 724 may be disposed on side surfaces of second set of texture features 714. Fourth set of texture features 724 is selected from the group consisting of flutes 716 and ribs 718, and combinations thereof. In the illustrated embodiments, flutes and ribs 716, 718 run vertically along the height of the side surfaces on the outside circumference of each microstructure comprising said second set of texture features 714. Fourth set of texture features 724 preferably include dimensions selected from a size within a range of about 1 micron to about 10 microns. Preferably, fourth set of texture features 724 are compression molded simultaneously with said first, second, and third sets of texture features into substrate 710.

Preferably, flutes and/or ribs 716, 718 with features and spacing larger than 1 micron are added to the exterior of the cylindrical pillars or cavities defining second set of texture features 714 to both add surface area and to increase structural resistance to bending and breaking. The spacing between individual microstructures of fourth set of features 714 is smaller for less viscous liquids and larger for more viscous liquids. Third set of texture features 720 cover both the tops of pillars and bottoms of cavities and the area between the pillars or cavities defining second set of texture features 714 in a substantially uniform manner. Together the second and third sets of texture features 714, 720 substantially increase the surface area exposed to the liquid covering the opposite surface from substrate 710.

Depending on the desired application, the first, second, third and fourth sets of texture features cooperate to increase the surface area of substrate 710 to effect at least one of adhesion, friction, hydrophilicity and hydrophobicity of substrate 710. In one embodiment, the substrate has a surface adhesion with a sliding friction force of greater than 50 gr/cm2 when applied against a surface comprised of a hydrophobic/hydrophilic mixture.

In a preferred embodiment, the substrate has a surface adhesion with a sliding friction force of about 325 gr/cm2 when applied against a surface comprised of a hydrophobic/hydrophilic mixture. In early studies, the inventors characterized rose petal structures and observed a 'rolling hill' effect in microstructures. Additionally, smaller microstructures were noted as 'hairs' that seemed to contribute strongly to the superhydrophobic effect. In order to best simulate this scheme, the inventors created sinusoidal designs as set forth herein that could reproduce and improve upon rounded microstructure effects seen naturally, starting with a sinusoidal waveform substrate with features from 300 microns diameter and pitch of 100 microns. The dimensions for the third set of texture features include in one embodiment pillars having 3 micrometers diameter, 6 micrometers pitch, and 5 micrometers tall. The second set of texture features in one embodiment includes fluted microstructure pillars that are at least 35 micrometers in diameter, 35 micrometers tall, and 10 micrometers spacing. When overlapped together, the second and third sets of micro features are formed along an axis normal to the surface of the sinusoidal waveform features (see, e.g., FIGS. 5 and 6). These are also maintained multidimensionally over the round To improve the superhydrophobic effect found in nature with the rose petal, second set of texture features, e.g., 714 was added with 'fluted' or 'ribbed' features running down the side surface. These fluted and ribbed features that define fourth set of texture features 724 simulate the smaller, hair like microstructures of the rose petal to further promote hydrophobocity. Accordingly, each microstructure of said first, second, third and fourth sets of texture features 712, 714, 720 and 724 have a respective pitch, height/depth, and diameter, and wherein are arranged so that liquids penetrate between at least said first and second sets of texture features in a Wenzel fully wetted state when applied against a liquid covered surface to promote adhesion between substrate 710 and the adjacent surface.

Preferably, the sinusoidal waveform of first set of texture features 712 includes rounded peaks that facilitate pressure distribution across substrate 710 when pressed against a liquid covered surface. Preferably, second and third sets of texture features 714, 720 are uniformly distributed across the rounded peaks of first set of texture features 712 provide increased surface area to first set of texture features 712. The rounded peaks define areas of increased pressure when substrate 710 is applied against a liquid covered surface that promote a transition of liquid droplets from a suspended Cassie-Baxter state to a Wenzel fully wetted state among at least said first and second sets of texture features. In a preferred embodiment, first, second and third sets, e.g., 712, 714, 720 of texture features allow for liquid penetration to a Wenzel fully wetted state, while the fourth set of texture features 724 are constructed and arranged to maintain superhydrophobic characteristics. The function of the second and third sets of texture features 714, 720 is to create a large surfaces area simultaneously with spacing wide enough the viscous liquids can flow through the structure at low pressure. Low pressure in this application is defined in the context of the weight associated with liquid droplets being sufficiently to create a Wenzel fully wetted state to promote adhesion of substrate 710 to an adjacent liquid covered surface. Accordingly, the microstructured surfaces of the present invention are designed to facilitate transitions from a Cassie-Baxter suspended droplet state to the Wenzel fully wetted state with a water droplet of greater than 10 texture liters in size.

One function of the sinusoidal waveform of first set of texture features 12 is to further increase the surface area while creating areas of increased pressure at the peaks of the features. These areas of increased surface area wet first, causing a rapid transition from the Cassie-Baxter suspended droplet state to the Wenzel fully wetted state. A second function of the sinusoidal waveform of first set of texture features, e.g., 612 is to keep the peak pressure low enough and to spread the pressure such that there is little or no penetration through the liquid layer on the surface into the underlying material. The second and third sets of texture features 614, are spread uniformly over the sinusoidal waveform of first set of texture features 612 and are normal to the curve of the surface. That is they are perpendicular to a surface tangent at each point of the microstructure on surface. This ensures that the maximum surface area is created in a structure that can be molded.

Figure 9:
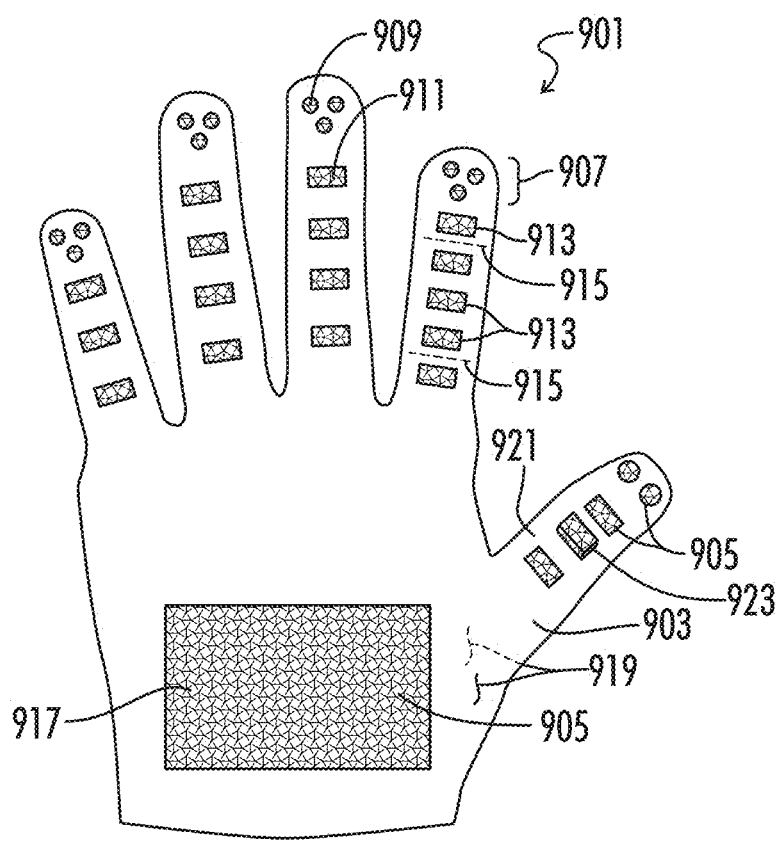
FIG. 9 depicts a garment, in particular a glove, with a microtextured hydrophobic/hydrophilic surface of the present invention

FIG. 9 depicts a glove, such as a surgical glove, having a hydrophobic/hydrophilic surface of the invention. A surgical glove 901 is comprised of an elastic material 903 comprised of textured islands 905. The detailed structure of textured islands 905 are given in FIGS. 1-8. The textured islands 705 are placed at positions 707 essential to grasping and manipulating surgical devices and slippery tissue. The geometry of the island structures can be selected to be consistent with normal bending action and typical points of contact. For example, in the finger tip area the islands are circular 909. In regions where the fingers bend the islands are linear 911 and arranged parallel 913 to the line of finger bending 915. In the palm area where articulation is absent, a larger island 917 substantially covering the entire surface of the palm may be selected. The islands 5 may be on two sides 919 of the glove, so the gloves can be used ambidextrously. The islands 5 may be raised 923 or substantially flush with the untextured regions of the glove 921.

All references cited herein are hereby incorporated by reference in their entirety.

We claim:

1. An article comprising a microstructured surface capable of forming an adhesion to a contact surface wherein the microstructured surface comprises a plurality of microtextured islands each comprising a hierarchical pattern including at least a plurality of first microfeatures and at least a plurality of second microfeatures, the plurality of second microfeatures disposed about the plurality of first microfeatures, wherein the hierarchical pattern is configured to develop a hydrophobic/hydrophilic mixture when in contact with a liquid interface, such that the hydrophobic portion of the mixture associates with at least one of the plurality of first microfeatures or the plurality of second microfeatures, and the hydrophilic portion of the mixture associates with the microfeatures that do not develop the hydrophobic portion, and wherein adhesion occurs when the shear stress exceeds a normal force and the microstructured surface comprises a hysteresis angle of greater than 5 degrees.

2. The article of claim 1, wherein at least a portion of the microstructured surface has a surface area at least twice the area of a smooth plane of same size.

3. The article of claim 1, wherein the hydrophobic/hydrophilic mixture comprises oil or air.

4. The article of claim 1, wherein the plurality of first microfeatures have a height and a width of from about 10 to about 100 microns and have a height:width aspect ratio of less than 5.

5. The article of claim 4, wherein the geometry of said plurality of first microfeatures is selected from a) a two-dimensional sinusoid, b) a cylinder, and c) a fin.

6. The article of claim 4, wherein the interface between said hierarchical pattern and said hydrophobic/hydrophilic mixture is a Wenzel-Cassie type interface.

7. The article of claim 1, wherein the article comprises a glove.

8. The article of claim 1, wherein the hydrophobic/hydrophilic mixture comprises air and aqueous solution.

9. The article of claim 1, wherein the hydrophobic/hydrophilic mixture comprises oil and aqueous solution.

10. The article of claim 1, wherein the hydrophobic/hydrophilic mixture comprises oil and air.

11. The article of claim 8, wherein the hydrophobic portion of the mixture traps air between the microstructured surface and the interface and the hydrophilic portion of the mixture does not trap air, and the resulting adhesion to the contact surface generates the contact hysteresis angle of greater than 5 degrees.

12. The article of claim 9, wherein the hydrophobic portion of the mixture traps oil between the microstructured surface and the interface and the hydrophilic portion of the mixture does not trap oil, and the resulting adhesion to the contact surface generates the contact hysteresis angle of greater than 5 degrees.

13. An article comprising a microstructured surface formed on a thin film capable of generating adhesion via a liquid interface to a contact surface wherein the microstructured surface comprises a plurality of microtextured islands each comprising a hierarchical pattern including at least a plurality of first microfeatures and at least a plurality of second microfeatures, the plurality of second microfeatures disposed about the plurality of first microfeatures, wherein the hierarchical patters is configured to develop a hydrophobic/hydrophilic mixture when in contact with the liquid interface, such that the hydrophobic portion of the mixture associates with at least one of the plurality of first microfeatures or the plurality of second microfeatures, and the hydrophilic portion of the mixture associates with the microfeatures that do not develop the hydrophobic portion, and wherein adhesion occurs when the shear stress exceeds a normal force and the microstructured surface comprises a hysteresis angle of greater than 5 degrees.

14. The article of claim 13, wherein at least a portion of the microstructured surface has a surface area at least twice the area of a smooth plane of same size.

15. The article of claim 13, wherein the hydrophobic/hydrophilic mixture comprises oil or air.

16. The article of claim 13, wherein the plurality of first microfeatures have a height and a width of from about 10 to about 100 microns and have a height:width aspect ratio of less than 5.

17. The article of claim 16, wherein the geometry of said plurality of first microfeatures is selected from a) a two-dimensional sinusoid, b) a cylinder, and c) a fin.

18. The article of claim 16, wherein the interface between said hierarchical pattern and said hydrophobic/hydrophilic mixture is a Wenzel-Cassie type interface.

* * * * *